United States Patent [19]
Goldberg

[11] Patent Number: 5,888,203
[45] Date of Patent: Mar. 30, 1999

[54] BIAXIAL LIGAMENTOUS-RESTRAINED PROSTHESES FOR UPPER AND LOWER EXTREMITY ARTHROPLASTIES

[76] Inventor: Robert Goldberg, 1250 N. Dearborn St., Apt. #5A, Chicago, Ill. 60610

[21] Appl. No.: 871,343

[22] Filed: Jun. 9, 1997

Related U.S. Application Data

[63] Continuation-in-part of Ser. No. 401,448, Mar. 9, 1995, Pat. No. 5,702,468.

[51] Int. Cl.⁶ ..................................... A61F 2/42
[52] U.S. Cl. ................... 623/21; 623/18; 623/20
[58] Field of Search ................... 623/16, 21, 18, 623/20

[56] References Cited

U.S. PATENT DOCUMENTS

| | | |
|---|---|---|
| 3,593,342 | 7/1971 | Niebauer . |
| 3,745,590 | 7/1973 | Stubstad . |
| 3,924,276 | 12/1975 | Eaton . |
| 3,973,277 | 8/1976 | Semple et al. . |
| 4,149,277 | 4/1979 | Bokros . |
| 4,164,793 | 8/1979 | Swanson . |
| 4,198,712 | 4/1980 | Swanson . |
| 4,450,591 | 5/1984 | Rappaport . |
| 4,936,854 | 6/1990 | Swanson . |
| 4,936,860 | 6/1990 | Swanson . |
| 4,955,915 | 9/1990 | Swanson . |
| 4,969,908 | 11/1990 | Swanson . |

FOREIGN PATENT DOCUMENTS 1533685  12/1989  U.S.S.R. ................................. 623/21

*Primary Examiner*—Michael J. Milano
*Attorney, Agent, or Firm*—Laff, Whitesel, Conte & Saret, Ltd.

[57] ABSTRACT

Surgically implantable bone prostheses comprising one or more biocompatable, medically inert contoured body members designed to be restrained along at least two crisscrossing axes and including at least one channel passing through the prostheses.

53 Claims, 8 Drawing Sheets

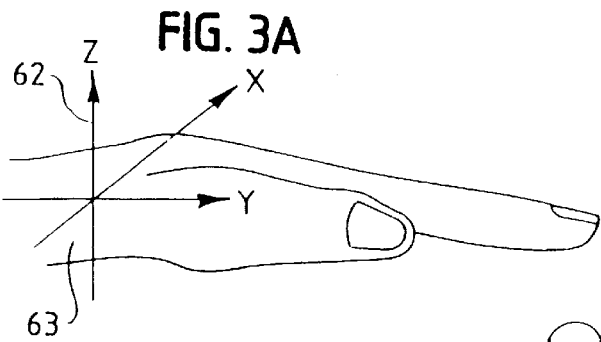
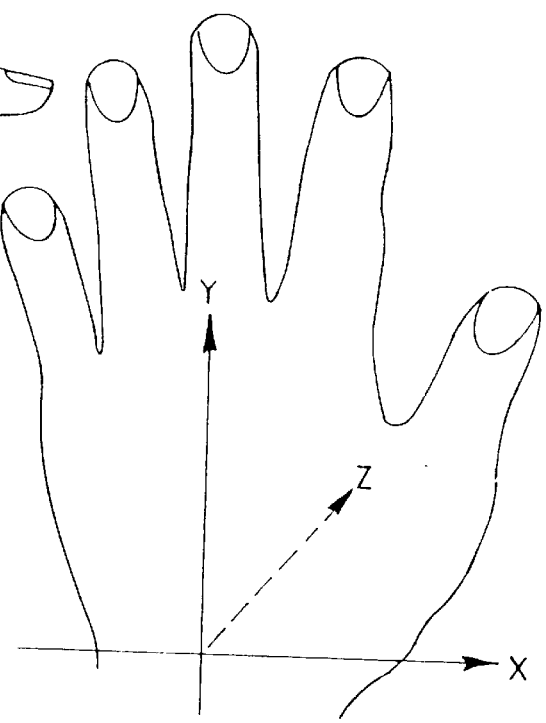
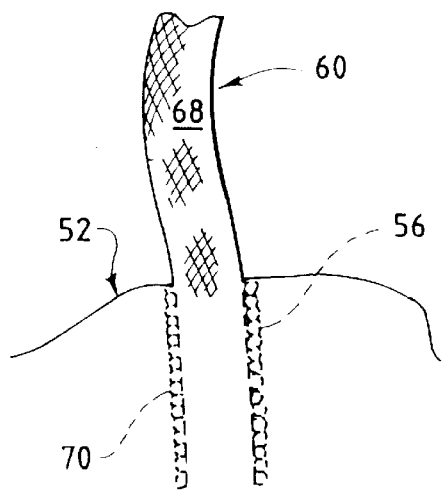
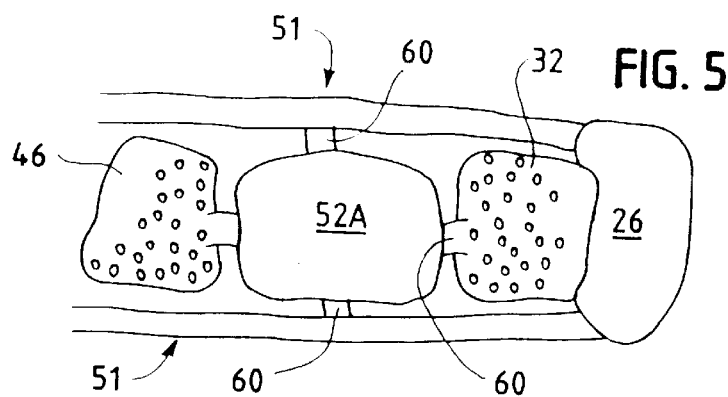
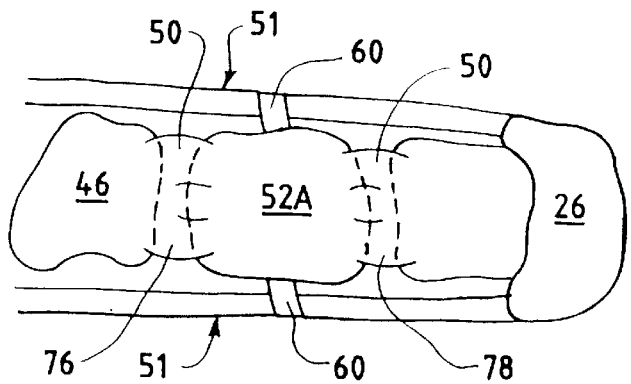

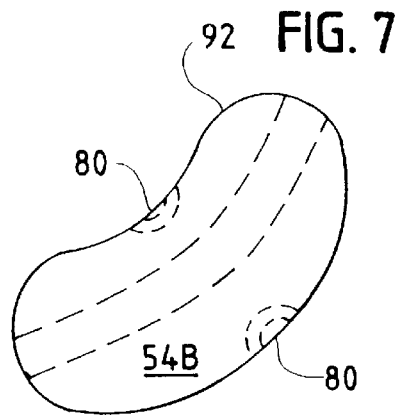
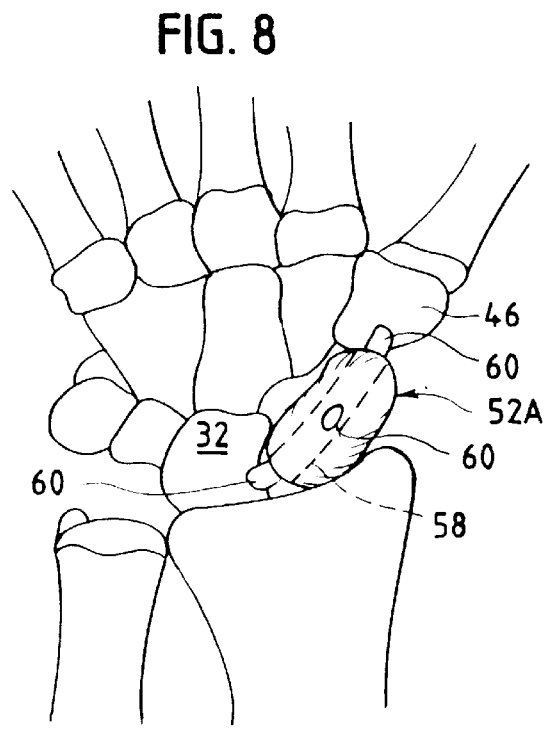
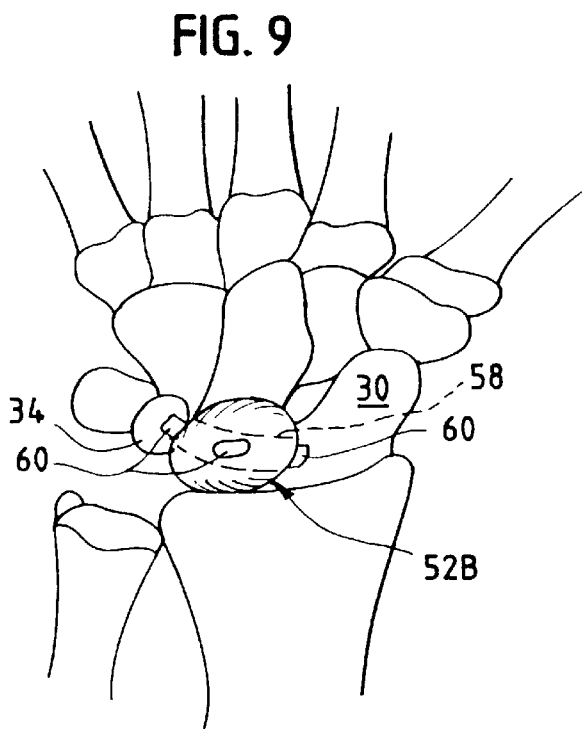

BIAXIAL LIGAMENTOUS-RESTRAINED PROSTHESES FOR UPPER AND LOWER EXTREMITY ARTHROPLASTIES

This is a continuation-in-part of application Ser. No. 08/401,448 filed Mar. 9, 1995 now U.S. Pat. No. 5,702,468.

FIELD OF THE INVENTION

This invention relates to prostheses. More particularly, this invention relates to new prostheses and methods for safely and effectively performing upper and lower extremity arthroplasties by tethering, suspending, and restraining prostheses using ligamentous means disposed along at least two crisscrossing axes.

BACKGROUND OF THE INVENTION

Implants or prostheses are employed for restoring damaged upper and lower extremity bones such as fingers, wrists, elbows, knees and ankles of human patients. These implants are especially useful in the reconstruction of joints which, for example, have been damaged by pathological conditions such as rheumatoid arthritis, degenerative arthritis, aseptic necrosis, and for treating trauma which may have a debilitating effect on articular joints.

Unfortunately, some joint implant designs available currently or described in the past have drawbacks arising from their construction and from the fact that they act merely as spacers for replacing damaged bones. For example, current and past scaphoid and lunate carpal bone replacements are generally undesirable, primarily because they cannot reproduce the normal and vital ligamentous restraints.

Joint replacement designs which rely on mechanical restraint mechanisms of various types (e.g. semi-constrained elbow arthroplasty) and degrees, also fail to simulate or replace ligamentous and capsular restraint along multiple axes. Many arthroplasties attempt to change the native biomechanical properties of the replaced joint instead of reproducing those native properties. For example, current total wrist arthroplasties replace a "link" system with a "hinge" system. Such biomechanical design substitutions have been deemed acceptable only because until now it has not been possible to satisfactorily reconstruct ligaments to joint replacements to achieve the native biomechanical properties of the replaced joint.

There are three types of arthroplasties: 1) unconstrained, 2) semi-constrained and 3) fully constrained. There is a precarious balance between the advantages of unconstrained designs (reduced bone-prosthesis loosening and fracture), and their disadvantages (subluxation and dislocation of the prosthesis and joint). The inherent advantage of a fully constrained device is stability (reduced subluxation and dislocation), whereas, the disadvantage is that most of the vector forces are transferred to the prosthesis-bone interface. This frequently results in loosening or fracture of the bone or of the prosthesis itself.

Semi-constrained devices have historically employed a variety of biomechanical mechanisms attempting to minimize the disadvantages of both unconstrained and fully constrained implants. Examples of semi-constrained implants are total elbow arthroplasties with the so-called "sloppy hinge". The common flaw with all of these current joint replacement designs is the inability to reconstruct and re-attach the replaced joint's vital capsular and ligamentous restraints, which dictate, in large measure, the behavior and stability of the joint.

Every joint has its own unique biomechanical properties which are dictated by the shape of the articulating bones/cartilage, by its function, and most importantly, by its capsular ligamentous three-dimensional restraints. To date, no joint replacement prosthesis has been designed to successfully reconstruct those vital ligamentous/capsular restraints to or through the replacement prosthesis in two or more axes. Restraining a prosthesis in two or more crisscrossing axes, as discussed below, has the mechanical effect of minimizing unwanted transitional and shear forces, while permitting the desired rotational motions necessary for the replaced joint.

This should be distinguished, for example, from implants using two parallel (rather than crisscrossing) channels to hold a "spacer" prosthesis A in position, as illustrated in FIG. 16. The biomechanical result of such an arrangement is the illustrated excessive translation and rotation of the "spacer" along the parallel channels with its potential clinical sequelae of wear debris, chronic instability of the prosthesis, and finally progressive arthritis.

The present invention may apply to any synovial or diarthroidial human joint. However, the preferred application of the invention is to joints whose motion is both quantitatively and qualitatively significant and therefore functionally important.

The definitions of "joints" and "articulations", adopted from *Stedman's Medical Dictionary*, 1982, pp. 126–7 and p. 737 refer to three types of "articulations": fibrous, cartilogenous, and synovial. The synovial articulation is the preferred application of this invention. A synovial articulation (or diarthrodial joint) is a joint allowing various amounts and types of motion in which the bony surfaces are covered with a layer of hyaline or fibrous cartilage. There is a joint cavity containing synovial fluid and lined with a synovial membrane, reinforced by a fibrous capsule and by ligaments.

In order to better explain the vital importance of the capsular and ligamentous restraints in a synovial joint, and to illustrate the flaws of arthroplasties which do not reconstruct these native restraints, the wrist carpal bones will be discussed below. This discussion will illustrate the anatomy, function and kinematics of the carpus with an emphasis on demonstrating the necessity and unique contribution of the invention as it applies to replacing the scaphoid and lunate carpal bones. The invention, however, is not limited to scaphoid and lunate prostheses but rather extends to all upper and lower extremity arthroplasties in any synovial or diarthroidial joints which are functionally important.

Wrist movement is apportioned between the radiocarpal and midcarpal joints in a very complex manner. The carpus, as discussed above, is biomechanically a link system, not a hinge system, like the knee. Accordingly, it is essential that a carpal implant reproduce the natural synchronous link system motion between it and the adjacent carpal bones to maintain the normal kinematics of the carpus. This serves to preserve the shape of the implant and to prevent wear, fracture, dislocation and particulate synovitis. In other words, synchronous motion of a carpal implant will help maintain normal kinematics of the remaining carpal bones and thus prevent global carpal instability and resultant surrounding arthritis.

The carpal implants most commonly available in the past have been made from silicone. Unfortunately, there are serious potential complications associated with the use of silicone in this and other medical applications. Indeed, since the scaphoid and lunate bones and their restraining ligaments are the most mechanically stressed, they are particularly susceptible to injury and complications. Thus, it is not surprising that it has been commonly reported in the literature that patients who have had silicone carpal implants experience silicone-related complications. These complications included subluxation and dislocation of the prosthesis, fragmentation and fracture of the prosthesis, and finally foreign body giant cell synovitis and focal carpal bone destruction.

Synovitis, mentioned above, is inflammation of the synovial membrane which lines and lubricates the wrist joint. It causes pain and inhibits wrist movement in bone joints. Violation of silicone implants with suturing techniques may contribute to fragmentation, debris and silicone-induced synovitis.

Focal carpal bone destruction is yet another complication which can arise at a later stage as a result of abnormal kinematics and synovitis over an extended period of time. Fragmentation and fracture of silicone implants and the resulting presence of silicone particulate debris results from implant stress related to implant translation subluxation or from implant fracture.

Finally, subluxation is a partial dislocation of the carpal bones. Subluxation and complete implant dislocation are complications which may result from the inherent lack of restraint of current carpal implants to their adjacent carpal bones and to the wrist capsule. In the native carpus, restraint is by way of ligaments and capsule. Thickenings of the palmer and dorsal capsule have been anatomically designated as quasi-discrete ligaments called "extrinsic ligaments" (e.g., radios-capho-capitate ligament). Whereas, those truly discrete interosseous ligaments which directly attach one carpal bone to another are called "intrinsic ligaments" (e.g. scapholunate ligaments). The intrinsic and extrinsic ligaments act dependently to synchronize the complex and balanced intercarpal kinematics. Currently available implants, including those made of both silicone and titanium alloys, do not reproduce the restraining mechanisms of both the intrinsic and extrinsic ligaments, and therefore these prostheses are subject to subluxation and complete dislocation.

To date, a satisfactory technique for reconstruction of intercarpal ligaments and capsular restraints incorporating carpal replacements has not been achieved. While the present invention is uniquely designed to allow the surgeon to accurately and predictably reconstruct the necessary ligamentous restraints and thus prevent the above-mentioned causes of failure, the prior art fails to meet this need.

For example, in U.S. Pat. No. 3,745,590 an implant is disclosed which includes parallel ligamentous elements (defining a single plane) molded into the body of a prosthesis at approximately opposite ends of its top surface. The ligamentous elements are either sutured to adjacent collateral ligaments, tied to the nearest adjacent carpal bone, or tied to an incised ligament or tendon. These ligamentous elements attach the prosthesis along a single axis and the implant is therefore restrained in only one plane. This lack of dual axis restraint may result in subluxation and increased shear.

The carpal metacarpal implant shown in the above-referenced '590 patent includes a stem portion that is integrally formed with the implant body and is adapted to fit into the medullary space in the metacarpal bone to be repaired. This implant includes at least one integral ligamentous element which can be tied or otherwise attached to an adjacent bone, ligament, or tendon. If the implant body includes more than one ligamentous element, the elements extend from a single opening along one edge of the implant body and are similarly tied to adjacent tissues, as described in relation to the first carpal implant above. This embodiment also only restrains the prostheses along a single axis.

Yet another carpal implant is shown in U.S. Pat. No. 4,198,712. This implant includes a stabilizing stem that extends outwardly and generally perpendicularly to the surface of the implant. The stem is adapted to be inserted into an adjacent carpal bone for stabilizing the implant postoperatively. Wires or sutures may be used in conjunction with the stem for temporary fixation and enhanced stabilization of the implant during the early healing process. The wires or sutures are passed through the implant into adjacent carpal bones. The stem and the wires or sutures are intended to restrain the prosthesis along a single axis. Also, as noted earlier, suturing directly into silicone is disfavored as generally it is believed to avulse, trailing silicone debris and potentially leading to silicone synovitis.

Accordingly, an object of the present invention is to provide a method and prostheses for safely replacing upper or lower extremity bone(s) in a joint of a human.

It is another object of the present invention to provide prostheses for replacing upper or lower extremity bone(s) of a joint in which the prostheses are suspended, tethered, and restrained along multiple axes.

It is yet another object of the present invention to provide prostheses for replacing upper or lower extremity joint bone(s) in which the reconstruction of effective restraint means encourages normal global kinematics.

It is a further object of the present invention to provide a method and prostheses for replacing upper or lower extremity joint bone(s) which involves suturing ligamentous means to adjacent capsules and bones, by way of native ligaments, or directly into bone using woven fabric, native capsule, bone-capsule-bone graft, or tendon.

It is yet another object of the invention to provide prostheses with select areas of inset ingrowth surface and/or surface coating to encourage limited ingrowth adhesion to surrounding capsular or ligamentous tissue.

Still another object of the invention is to provide a method for stabilizing a prosthesis while drawing it to and maintaining it directly against an adjacent native capsule to facilitate natural ingrowth adhesion of surrounding capsular or ligamentous tissue into the implant surface to both facilitate anchorage of the implant body directly to native capsular and ligamentous tissue while providing further global stabilization and improved kinematics.

These and other objects and advantages of the invention will appear hereinafter.

SUMMARY OF THE INVENTION

The present invention accomplishes the foregoing objects by providing a prosthesis comprising a body member and crisscrossing ligamentous means.

The crisscrossing ligamentous means, as described below, inhibit translation and spin on all three dimensional axes (x, y and z). This is illustrated in FIG. 16 which depicts the biomechanical result of using parallel channels in a "spacer" prosthesis A. FIG. 17, in contrast, shows the inhibition of translation and rotation of a prosthesis B tethered and suspended in accordance with the present invention. As discussed below, the suspended prosthesis may be attached so that it is buttressed to adjacent capsule.

The body member is made totally or partially from any appropriate biocompatible, medically inert material such as a ceramic, titanium, stainless steel alloys, or a non-ceramic substrate with a ceramic or other biocompatible, medically inert coating. It is contoured to resemble the shape of the bone which it replaces.

In the preferred embodiment, the body member includes at least two non-intersecting channels which pass through the body member in a crisscross fashion with the axes of at least two of the channels lying in different planes so that ligamentous means disposed in those non-intersecting channels will be biomechanically independent. It is further preferred that only two channels be used and, whether intersecting or not, that the channels be substantially perpendicular. In less preferred embodiments, all of the channels may be in direct communication, that is, they may physically intersect; it is preferred that at least two of the channels be substantially perpendicular in these embodiments as well.

In a further alternative embodiment, at least one channel passes through the body member and at least one channel passes through contiguous bones and cartilage in a crisscross fashion (preferably substantially perpendicular) to the first channel. Obviously, the channel(s) passing through contiguous bones and cartilage will not intersect with channel(s) passing through the body member. The channel through the contiguous bones and cartilage will be made by conventional means.

Selected surface areas of the body member may be made receptive to tissue ingrowth to facilitate and encourage area specific ingrowth adhesion of surrounding capsular or ligamentous tissue. Such ligamentous ingrowth zones are selected based on the anatomic native "non-articular" surfaces of the replaced bone, since native non-articular surfaces, relatively void of articular cartilage, provide the native pathway for anatomic attachment of ligament/capsule to that bone. Ligamentous ingrowth zones may be provided by fabricating specifically designed porosities in the surface of the body member in those areas. These ingrowth zones would generally correspond to the native non-articular anatomic surfaces or zones of any given bone where ligaments and capsules naturally attach in-vivo.

Tissue ingrowth, as discussed immediately above, may be facilitated by drawing the body member up against adjacent capsule, or "buttressing" it. This reduces movement of the body member while tissue ingrowth proceeds.

In one embodiment, the ligamentous means are not secured either to one another or otherwise within the channels before implantation. Rather, as discussed below, the body member is allowed minimal gliding motion on each ligamentous means while the combined effect of two or more ligamentous means is to tether and suspend the body member to prevent significant translation of the body member.

In another alternative embodiment in which the channels in the body member physically intersect, the ligamentous means are first attached to each other near their midpoints and the pre-attached ligamentous means are mounted in the intersecting channels. It is further preferred that the point of attachment of the ligamentous means be positioned at the point of intersection of the channels.

The ligamentous means may be native or artificial, and porous or non-porous. In one preferred embodiment, the ligamentous means comprise a porous woven fabric which is tissue ingrowth receptive for affixation to adjacent tissues by tissue ingrowth. Alternatively, native tissue such as capsular strips, bone-capsule-bone-graft, or tendon, for example, may be used as the ligamentous means. This would enhance affixation of the graft to surrounding bone. The ligamentous means preferably are affixed to the adjacent bones by way of remaining ligament or by affixing the ligamentous means into the surrounding native cancellous bone itself. The volume of the bone portion of bone capsule bone grafts may be enhanced with synthetic bone pastes such as Norian®.

The ligamentous means may be positioned for suspending the prosthesis along at least two crisscrossing, preferably substantially perpendicular axes, thereby restraining the body member to limit translation and destructive shear of the implant while permitting limited necessary rotation of the body member in relation to adjacent bones. For example, the first restraining axis may be established when the prosthesis is attached to adjacent bones, while the second and subsequent restraining axes are established when the prosthesis is attached to the adjacent capsules. Alternatively, depending on the joint application, the ligamentous means may be affixed to only ligament and capsule without affiliation to bone.

Alternatively, the ligamentous means may be used to draw or buttress the body member up against adjacent capsule to limit movement of the body member in one or more directions, as illustrated diagramatically in FIGS. 18A and 18B in which a prosthesis 2 is represented suspended on crisscrossing ligamentous means 4 and 6 which are attached respectively to adjacent bones 8 and 10 and adjacent capsule 12 and 14. Sutures 16 and 18 are used to affix the ligamentous means to the adjacent capsule. Thus, in FIG. 18A, the prosthesis is suspended along two crisscrossing axes (corresponding to the ligamentous means) but spaced from adjacent bone and capsule. In FIG. 18B, however, the prosthesis is also buttressed to adjacent capsule at points A and B. This type of tethering or attachment of the body member to limit movement in one or more directions will be indicated in certain circumstances, including but not limited to circumstances where ligamentous ingrowth zones are provided on certain surfaces of the body member.

The above, as well as other objects and advantages of the invention, will become apparent from the following detailed description of the preferred embodiments as illustrated in the accompanying drawings.

BRIEF DESCRIPTION OF THE DRAWINGS

FIGS. 3A–3B are respectively side and top views of a human hand and wrist illustrating the positioning of the perpendicular x,y and z axes;

FIG. 4 is a partial cross-sectional view of the prostheses of FIG. 2, illustrating the affixation of the ligamentous means within a channel by tissue ingrowth;

FIG. 5 is a partial side view of a scaphoid prosthesis, illustrating the affixation of the ligamentous means to adjacent carpal bones;

FIG. 6 is a partial side view of a scaphoid prosthesis, illustrating the affixation of the ligamentous means to adjacent carpal ligaments;

FIG. 7 is an alternate embodiment of the prosthesis of FIG. 2A in which ligamentous means are secured by means of eyelets;

FIG. 8 is a plan view of a scaphoid prosthesis subsequent to its implantation in the wrist;

FIG. 9 is a plan view of a lunate prosthesis subsequent to its implantation in the wrist;

DETAILED DESCRIPTION OF THE INVENTION

Lunate and scaphoid carpal bone prostheses are described below in order generally to illustrate the application of the invention. One skilled in the art will readily discern from the lunate and scaphoid carpal bone examples methods for safely and effectively performing upper and lower extremity arthroplasties using my new prostheses which are tethered, suspended, and restrained along multiple axes by ligamentous means. Thus, although each human joint has its own unique shapes and kinematic properties, the principles of the present invention embodied in the lunate and scaphoid carpal bone arthroplasties are applicable to any synovial or diarthroidial joint.

Figure 1:
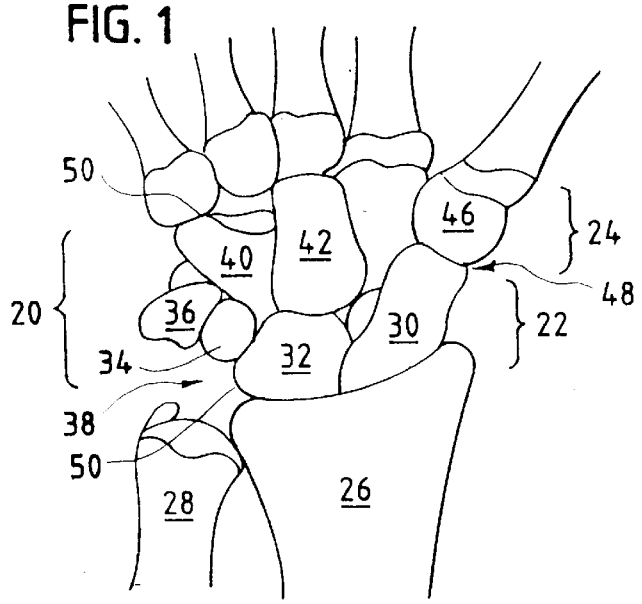
FIG. 1 is a plan view of the anterior or palmar side of the bones of the wrist joint of the right hand, shown palm up.

Referring generally to FIG. 1, an anterior or palmar side of the bones of the wrist carpus 20 of a right hand is shown. The bones that form the carpus of the wrist 20 include a proximal carpal row 22 and a distal carpal row 24. Proximal carpal row 22 is adjacent the radius 26 and the ulna 28 of the wrist and includes a scaphoid bone 30, a lunate bone 32, a triquetrum bone 34, and a pisiform bone 36. The radial carpal joint 38 is that space between the proximal carpal row 22 and the articulating distal radius 26. The distal carpal row 24 includes a hamate bone 40, a capitate bone 42, a trapezoid bone 44, and a trapezium bone 46. The midcarpal joint 48 of the wrist extends between the distal and proximal carpal rows.

Figure 1A:
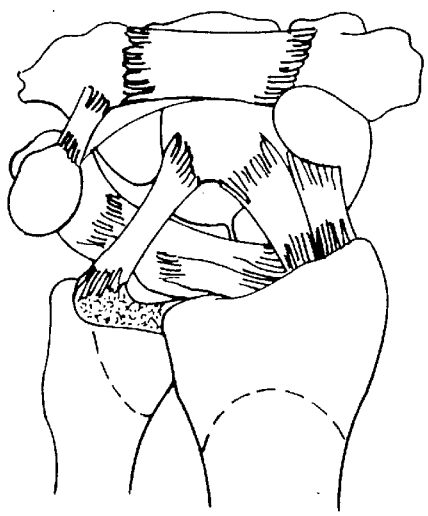
FIGS. 1A–1C are plan views respectively of the superficial palmar ligaments, the deep palmar ligaments and the dorsal ligaments.
Figure 1B:
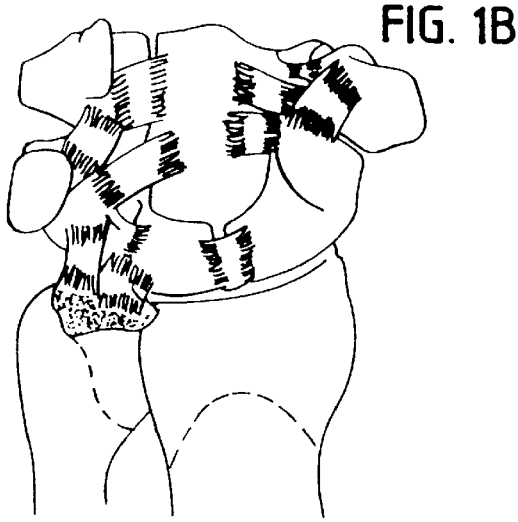
Figure 1C:
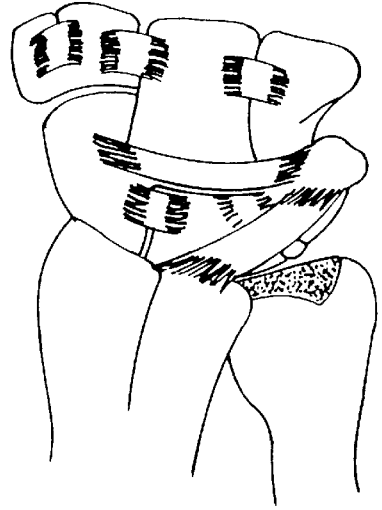

The extrinsic palmar carpal ligaments are shown in FIG. 1A, the intrinsic ligaments are shown in FIG. 1B and the dorsal extrinsic ligaments are shown in FIG. 1C. Normal wrist movement is very complex and involves, in part, motion at the midcarpal joint and in part motion at the radiocarpal joint. Additionally, there is a predicable well-orchestrated rotational motion specific and different for each carpal bone which is generated by the bone's shape and by its ligamentous and capsular attachments. For example, in radial deviation of the wrist the scaphoid distal pole rotates in a palmar direction, in a sense making "room" for the distal carpal row to pass over the proximal row. Likewise, in ulnar deviation the normal scaphoid rotates dorsally, away from the palm, tethered by its neighboring lunate and surrounding capsule, in a sense making "room" for the distal carpal row to pass more easily "under" the proximal row. In pathological conditions such as severe wrist sprains, the ligaments are disrupted and the synchronous carpal kinematics are impaired. This may lead to pain, arthritis and advanced collapse of the carpus, i.e., SLAC (Scapho-lunate advanced collapse) wrist. A similar fate of SLAC may occur secondarily to scaphoid fracture non-union or avascular necrosis. During the surgical replacement of a carpal bone (scaphoid or lunate) those ligaments which are not already disrupted must be cut. Unless those ligaments are reconstructed or substituted, the same fate may ensue: instability of the prosthesis, surrounding carpal arthritis and eventual carpal collapse. Too frequently this is the fate of current "unrestrained" carpal prostheses.

Figure 2A:
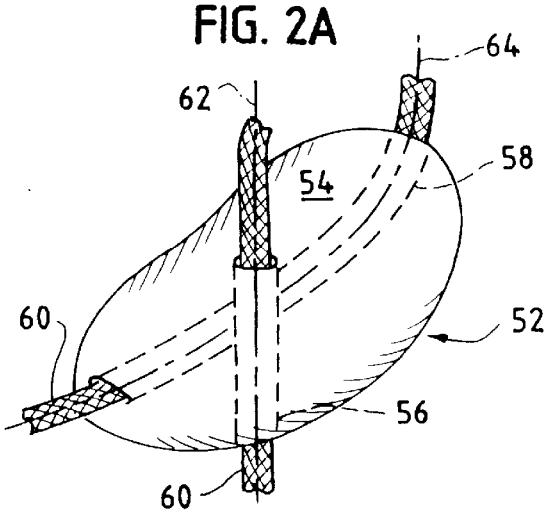
FIGS. 2A and 2B are perspective views of scaphoid and lunate carpal bone prostheses in accordance with the present invention.
Figure 2B:
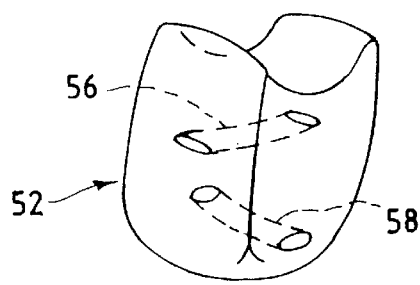

In accordance with the present invention, a "restrained" prosthesis, the complex carpal motion will be preserved and collapse with arthritis prevented. In FIGS. 2–6, the prosthesis is generally denoted by the numeral 52 and comprises a body member 54 contoured to resemble the shape of the carpal bone which it replaces. In FIGS. 2A and 2B, denoting respectively a scaphoid prosthesis and a lunate prosthesis, the body member includes first and second substantially perpendicular independent channels, 56 and 58, and ligamentous means 60 are positioned within the channels for tethering prosthesis 52 to adjacent tissues, including surrounding carpal bone and ligaments as well as dorsal and palmar capsule.

FIGS. 3A and 3B illustrate the three-dimensional structures of the carpus. The x, y and z geometric axes of the hand are shown as 90° perpendicular planes of reference. To maintain reproducibility, for example on an x-ray, the following anatomic landmarks are chosen to create these axes: The x-axis represents a best fit line between the ulnar and radial styloids on a PA view. The y-axis is a best fit line through the length of the 3rd metacarpal shaft. The z-axis is simply a plane perpendicular to both the x and y axes. By creating these axes one has a mathematical tool and language to describe any coordinate or direction within the carpus. For example, each channel within a given carpal prosthesis has definable coordination on the x, y and z axes.

Returning now to FIG. 2A and continuing with the example of the scaphoid prosthesis, first channel 56 may be said in this embodiment to lie on an imaginary tether axis 62, essentially the z axis (dorsal to palmer) in FIGS. 3A and 3B. The second channel 58 (FIG. 2A) may be said in this embodiment to lie slightly obliquely to the x and y axes, articulating with the trapezium and lunate. In the preferred embodiment illustrated, channel 58 is curved to correspond generally to the curvature of the body member i.e., along its long axis, proximal pole to distal pole. Also, in the illustrated embodiment, channel 56 is substantially perpendicular to channel 58, and the two channels intersect at a single point within the body member. In alternative embodiments, the channels need not be intersecting, nor need they be substantially perpendicular at every moment of the entire rotational arc of motion of the implanted invivo prosthesis. That is, in a kinematic analysis, as the implanted body member rotates during wrist motion, the ligamentous means will constantly change their vector alignment, relative to the body member.

In FIG. 2A, each ligamentous means 60 extends through first and second channels 56 and 58, and emerges from the openings at each end of the channels. In the illustrated embodiments, the channels may be ovoid in cross-section in order to protect the body member against stress risers. The edge of each channel opening may be rounded to remove any sharp interface against the ligamentous means. Nevertheless, if desired, the channels may be circular or of any other cross-sectional shape which preserves the above desirable characteristics. Also, the channels may be used without a porous coating or other affixation means or with a porous coating (70) to provide surface to facilitate tissue ingrowth between the ligamentous means and the prosthesis.

Ligamentous means 60 in FIG. 2A is placed through channels of the body member and is surgically attached to adjacent ligaments, capsule, or bone (see FIG. 4). Ligamentous means 60 may be made of Dacron or any other ingrowth receptive fabric (including Teflon), native tendon graft (e.g., palmaris longus), capsule, or bone-capsule-bone graft.

For example, when ligamentous means 60 are secured to an adjacent carpal bone (FIG. 5), various techniques may be used including suturing the ligamentous means directly to the adjacent intrinsic (interosseous) ligament. For example, ligamentous means 60 of a scaphoid prosthesis 52A could be sutured to the scaphotrapezial ligament 76 and the scapholunate ligament 78 which are located between trapezial bone 46 and scaphoid bone 30 (which has been replaced by prosthesis 52A) and scaphoid bone 30 (prosthesis 52A) and lunate bone 32, respectively, as shown in FIG. 6. An alternative technique would include removal of a very small area of cartilage and endosteum to expose raw cancellous bone. Drill holes would then be placed in the bone for passage of suture and a suture placed in the end of the ligamentous means. The suture would be passed through the drill holes pulling the ligamentous means firmly against, or through, the scarified bone and the sutures tied to each other in a horizontal mattress fashion. This technique of suturing is similar to that described by Julio Taleisnick, M.D. (*Journal of Hand Surgery*, 17A, March 1992, pages 354–359, "A Technique For Direct Repair of the Scapho-Lunate Interosseous Ligament"). An alternate technique to suture the ligamentous means to adjacent bone may include use of small bone anchors, e.g., Mitek® anchors which are available from Surgical Products, Inc. of Norwood, Mass., or to secure the ligamentous means by an interference screw. Similarly, the lunate prostheses could be secured by ligamentous means in a similar fashion to its adjacent carpal bones, i.e., scaphoid (and/or scapholounate ligament) and the triquetrum (and/or lunotriquetral ligament).

In a less preferred alternate embodiment, body member 54B includes one or both of the ligamentous means secured to its outer periphery 92 by means of eyelets 80 (FIG. 7) movably restraining the prosthesis to adjacent tissues.

In use, prosthesis 52 is surgically implanted into a wrist for replacing a damaged carpal bone using standard surgical procedures. If the native intrinsic and extrinsic ligaments are intact, they are divided as the damaged carpal bone is removed, preserving neighboring ligament and capsular attachments. The properly sized prosthesis is then inserted into and properly positioned within the space created by the excised carpal bone such that one axis of the ligamentous means 60 is oriented towards the palmar or dorsal capsule 51 (FIGS. 4–6). The prosthesis is next oriented along the second axis by inserting it in normal articulating alignment with its neighboring carpal bones. Those articulating ends represent the exits for the second tethering channel through which the ligamentous means have been placed. Finally, the ligamentous means are fixed to adjacent capsule and intrinsic (interosseous) ligament or bone (see FIGS. 4–6).

The following is a description of the method by which the ligamentous means through channel 56 is fixed to the dorsal and palmar capsule.

In this method, referring again to FIG. 2A, the ligamentous means through channel 58 attaching to bone substitute for the "intrinsic ligaments" (i.e., short interosseous ligaments), and the ligamentous means through channel 56 substitute for the extrinsic ligaments (i.e., dorsal and palmar capsular attachments). In order to secure ligamentous means through channel 56 sutures attached to the ligamentous means at each end may be sewn directly to capsule and at either or both ends. Alternatively, the suture may be brought through capsule, then skin, and tied down in a standard fashion over a button. After many weeks of healing the pull-out suture and button would be removed leaving the secured ligamentous means in place.

FIGS. 8 and 9 illustrate scaphoid and lunate prostheses, 52A and 52B, respectively, after to their implantation in a wrist. First referring to FIG. 8, scaphoid prosthesis 52A is tethered by ligamentous means 60 by way of channel 58, to trapezium bone 46 and lunate bone 32. Scaphoid prosthesis 52A is also tethered by a second ligamentous means 60 to the dorsal and palmar capsules by way of channel 56. This second ligamentous means would be substantially perpendicular to the plane of the Figure (i.e., in and out of the plane of the paper). Referring to FIG. 9, lunate prosthesis 52B is shown tethered by way of its two channels by ligamentous means 60 to scaphoid bone 30 and triquetrum bone 34 and by the other ligamentous means to the dorsal and palmar capsules. Again, this second ligamentous means is illustrated substantially perpendicular to the Figure.

FIGS. 10–15 are examples of the crisscrossing channel restraint of the present invention as it relates to some examples of hand and ankle joints in accordance with the present invention. These examples are not intended to be limiting of the invention in any way.

Figure 10:
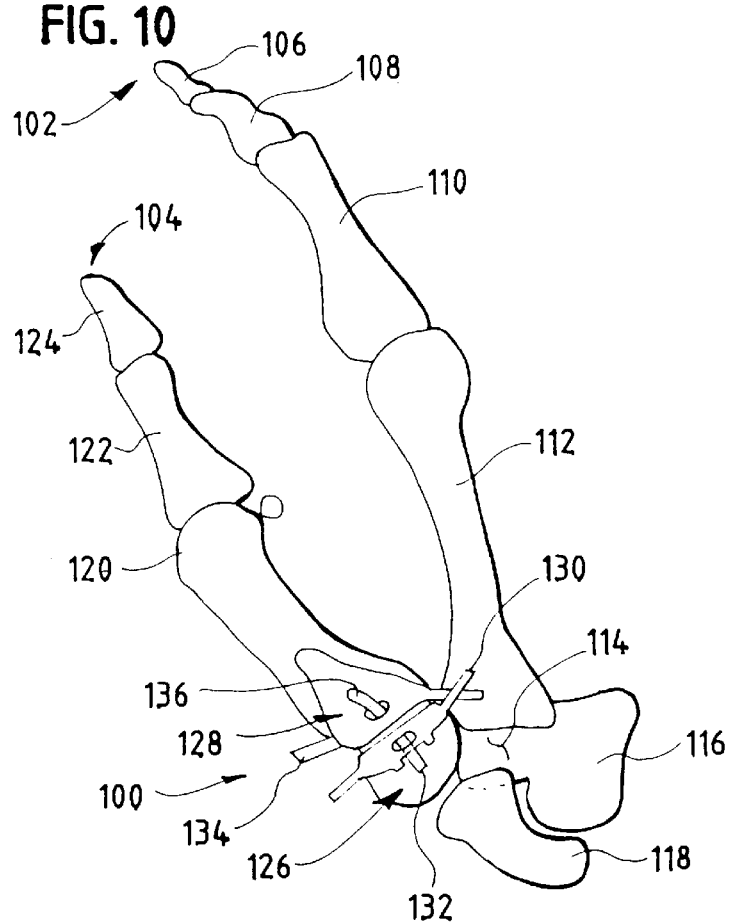
FIG. 10 is a plan view of the posterior side of selected bones of the right human hand illustrating a carpometacarpal prosthesis in accordance the present invention.

FIG. 10 illustrates a carpometacarpal biaxially restrained arthroplasty 100 in a right hand which, for purposes of illustration, shows only the index finger and the thumb. The following bones are illustrated in this figure:

| | |
|---|---|
| Index finger | 102 |
| Thumb | 104 |
| Index finger distal phalanx | 106 |
| Index finger middle phalanx | 108 |
| Index finger proximal phalanx | 110 |
| Index finger second metacarpal | 112 |
| Trapezoid | 114 |
| Capitate | 116 |
| Scaphoid | 118 |
| Thumb metacarpal | 120 |
| Thumb proximal phalanx | 122 |
| Thumb distal phalanx | 124 |

The carpometacarpal biaxially restrained arthroplasty 100 includes a hemi-trapezium component 126 and a metacarpal base component 128 which are respectively interference-fit (and optionally cemented) to preformed cavities in the trapezium and the thumb metacarpal bones. The trapezium arthroplasty illustrated here is a "hemi" or half-arthroplasty, incorporating two ligamentous means 130 and 132 which pass through intersecting crisscrossing channels in the trapezium arthroplasty and are attached, as appropriate, to surrounding ligaments (e.g., beak ligament), capsule and bone. Metacarpal base component 128 similarly includes two ligamentous means 134 and 136 which pass through crisscrossing intersecting channels and are attached, as appropriate, to surrounding ligaments, capsule and bone.

Figure 11:
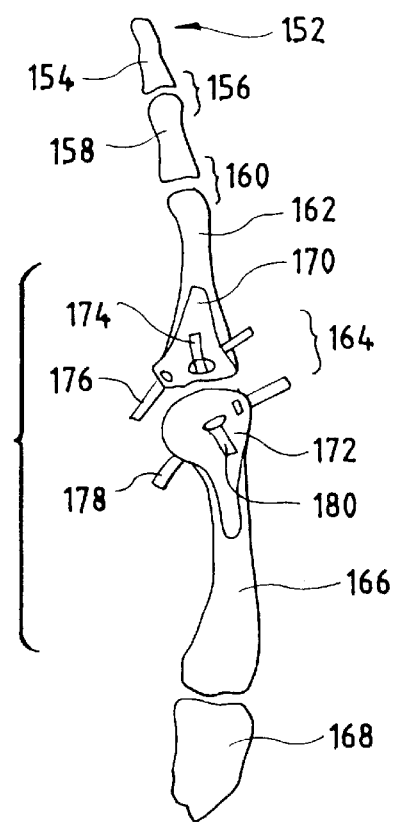
FIG. 11 is a side view of the fifth ray of the right hand illustrating a metacarpal-phalangeal arthroplasty in accordance with the invention of the right human hand.

FIG. 11 is a side view of the fifth ray of the right hand showing a two component metacarpal-phalangeal (MCP) prosthesis 150, utilizing the ligamentous means in accordance with the present invention. The following bones are illustrated in this figure:

|  |  |
|---|---|
| Fifth ray | 152 |
| Distal phalanx | 154 |
| Distal interphalangeal joint | 156 |
| Middle phalanx | 158 |
| Proximal interphalangeal joint | 160 |
| Proximal phalanx | 162 |
| Metacarpal-phalangeal joint | 164 |
| Metacarpal | 166 |
| Hamate | 168 |

The two components of the MCP arthroplasty are the proximal phalanx base component 170 and the metacarpal head component 172 which span metacarpal-phalangeal joint 164 and are inserted respectively in preformed cavities in the metacarpal and proximal phalanx bones. Pairs of crisscrossing ligamentous means are passed through channels 178 and 180 in metacarpal head component 172 and are attached, as appropriate, to surrounding ligaments and capsule.

Figure 12:
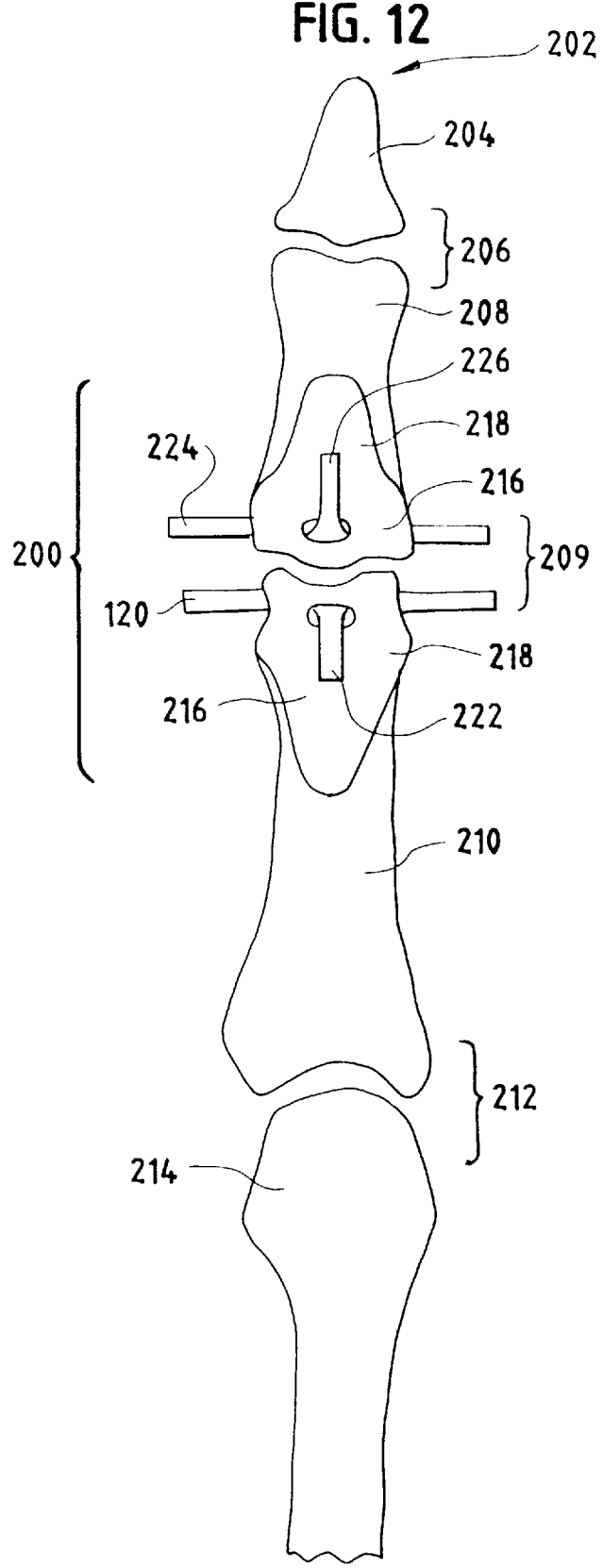
FIG. 12 is an anterior-posterior view of a finger proximal interphalangeal joint biaxially restrained arthroplasty in accordance with the invention.

FIG. 12 illustrates a finger proximal interphalangeal joint biaxially restrained arthroplasty. The body of this illustrated two-stemmed articulating prosthesis is ceramic, although other biocompatible materials can be used. The prosthesis is shaped to match the morphology of the base of the middle phalanx and head of the proximal phalanx, illustrating that the above described principles of the carpal prosthesis apply to the hand and finger joints.

The following bones and joints are illustrated in this figure, to establish the environment of the arthroplasty:

|  |  |
|---|---|
| Fifth ray | 202 |
| Distal phalanx | 204 |
| Distal interphalangeal joint | 206 |
| Middle phalanx | 208 |
| Proximal interphalangeal joint | 209 |
| Proximal phalanx | 210 |
| Metacarpal phalangeal joint | 212 |
| Metacarpal | 214 |

The two component proximal interphalangeal arthroplasty 200 includes middle phalanx base component 216 and proximal phalanx head component 218 which span proximal interphalangeal joint 209. Middle phalanx base component 218 includes crisscrossing ligamentous means 224 and 226 and proximal phalanx head component 216 includes crisscrossing ligamentous means 220 and 222.

Figure 13:
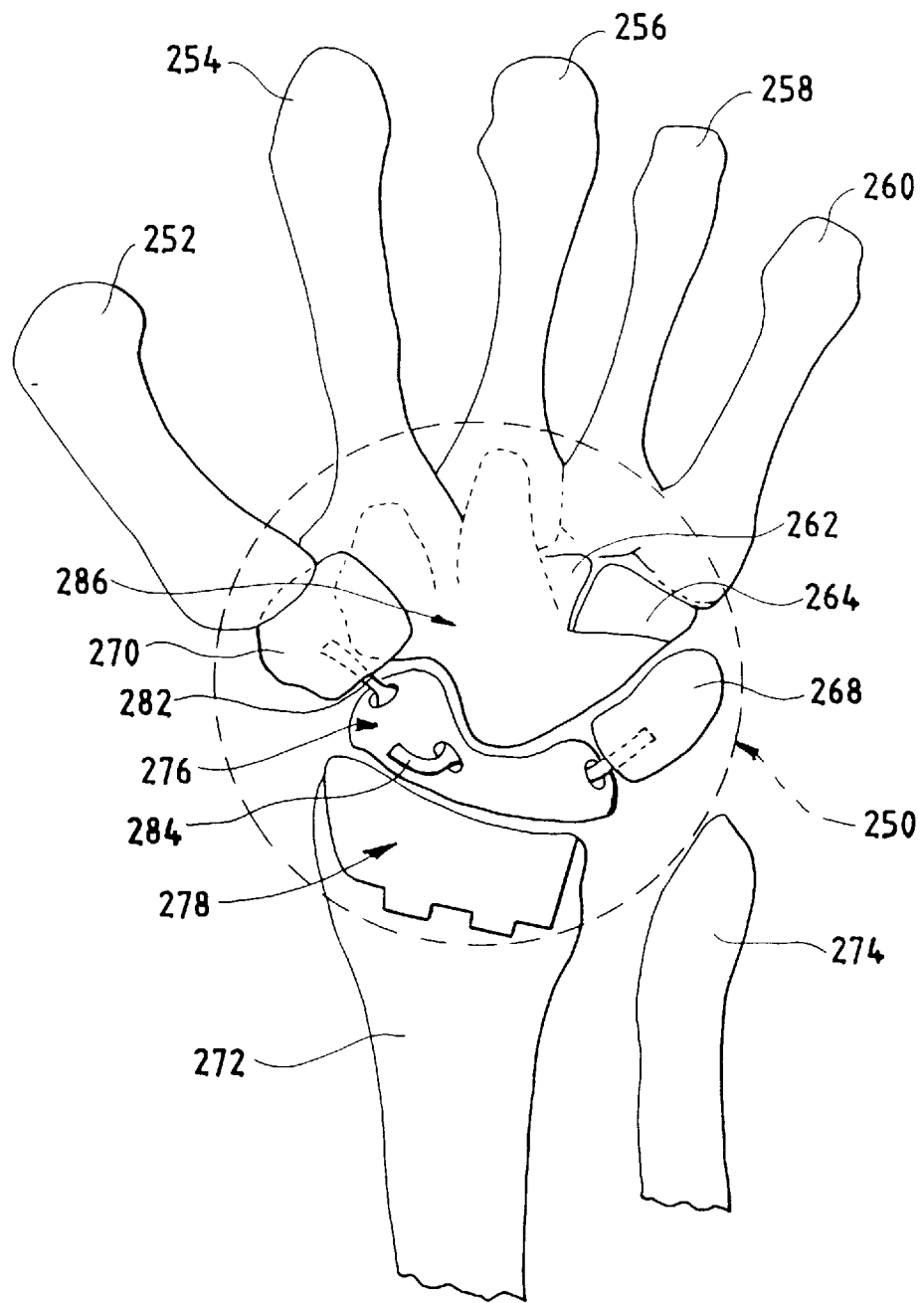
FIG. 13 is a plan view of a human hand showing a total wrist arthroplasty comprising a three component system in which the middle component, which replaces the scaphoid and lunate, employs a ligamentous reconstruction in accordance with the present invention.

FIG. 13 illustrates a unique three component total wrist arthroplasty in which the middle component is restrained in accordance with the present invention. In order to establish the emplacement of the arthroplasty, the following features of the wrist and its environs are shown:

|  |  |
|---|---|
| Thumb metacarpal | 252 |
| Metacarpal 2 | 254 |
| Metacarpal 3 | 256 |
| Metacarpal 4 | 258 |
| Metacarpal 5 | 260 |
| Capitate (majority removed) | 262 |
| Hamate (half removed) | 264 |
| Triquetrum | 268 |
| Trapezium | 270 |
| Radius | 272 |
| Ulna | 274 |

Total wrist arthroplasty 250 includes a proximal component 278, representing a replacement for the distal radius, which is fixed in place using conventional means including the formation of a receiving cavity in the radius and attachment by an interference fit, screws, bone ingrowth surface, and/or bone cement. The middle component 276, representing a combined scaphoid and lunate replacement, is tethered, suspended and restrained between the native triquetrum 268 and trapezium 270 via ligamentous means 284 in a channel through middle component 276. The ligamentous means are attached by conventional means (e.g., drilled holes and screws) to the native triquetrum and the trapezium. Ligamentous means 282 is attached to palmar and dorsal capsule (not shown), also by conventional means. The distal component 286, representing partial replacement of the distal carpal row is affixed to the remaining distal carpus and metacarpals using conventional means similar to those used to fix the proximal component. By employing a three component system, with the middle component suspended and restrained by ligamentous attachments, a native biomechanical "link" system is recreated which is superior to current two component designs which create an unnatural hinge system.

Figure 14:
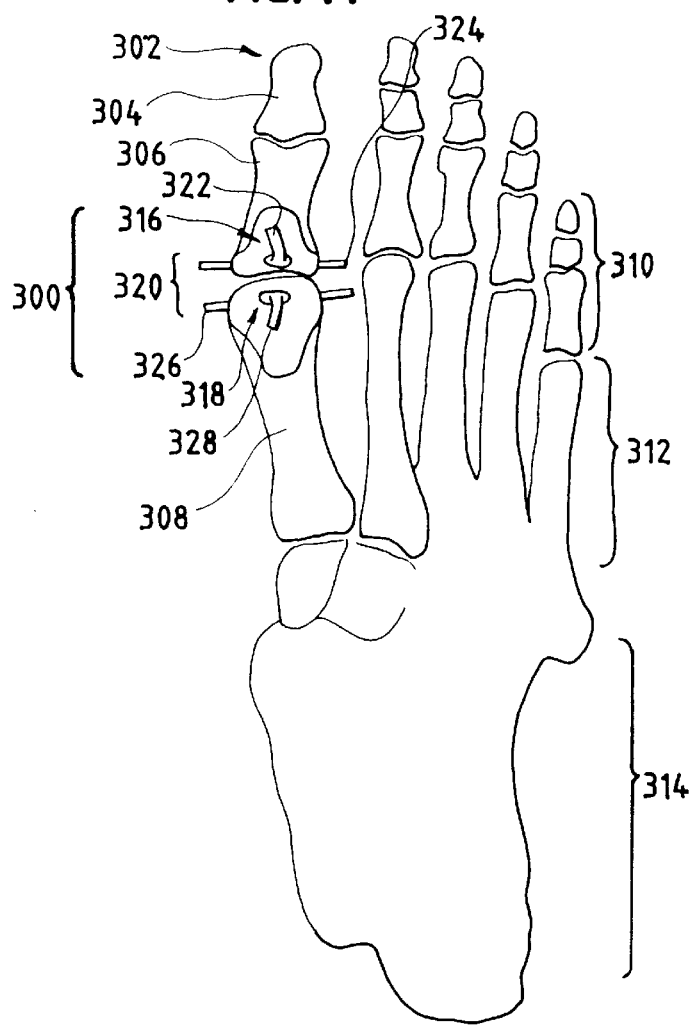
FIG. 14 is a dorsal view of the right human foot showing a hallux metatarsal-phalangeal biaxially restrained arthroplasty in accordance with the present invention.

FIG. 14 illustrates a hallux metatarsal-phalangeal biaxially restrained arthroplasty 300 in the right human foot. The bones of the foot which are pertinent to this discussion include:

|  |  |
|---|---|
| Hallux ("great toe") | 302 |
| Hallux distal phalanx | 304 |
| Hallux proximal phalanx | 306 |
| Hallux (first) metatarsal | 308 |
| Phalanges | 310 |
| Metatarsals 2–5 | 312 |
| Tarsal bones | 314 |

Biaxially restrained arthroplasty 300 includes two components, a proximal phalanx component 316 and a metatarsal head component 318 which span the metatarsal-phalangeal joint 320. Proximal phalanx component 318 includes ligamentous means 322 and 324. Metatarsal head component includes ligamentous means 326 and 328.

Figure 15A:
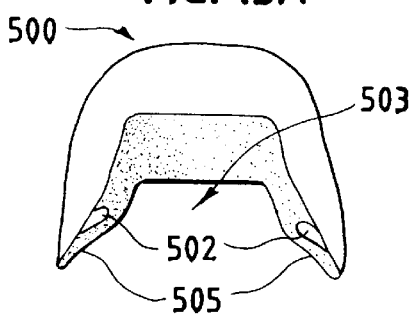
FIG. 15 is an anterior-posterior view of a metacarpal-phalangeal arthroplasty in which one of the two channels in the metacarpal component of the arthroplasty is drilled entirely through the metacarpal bone.
Figure 15B:
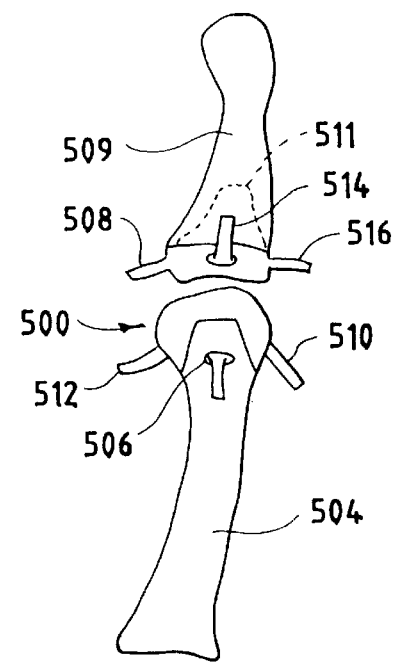
Figure 16:
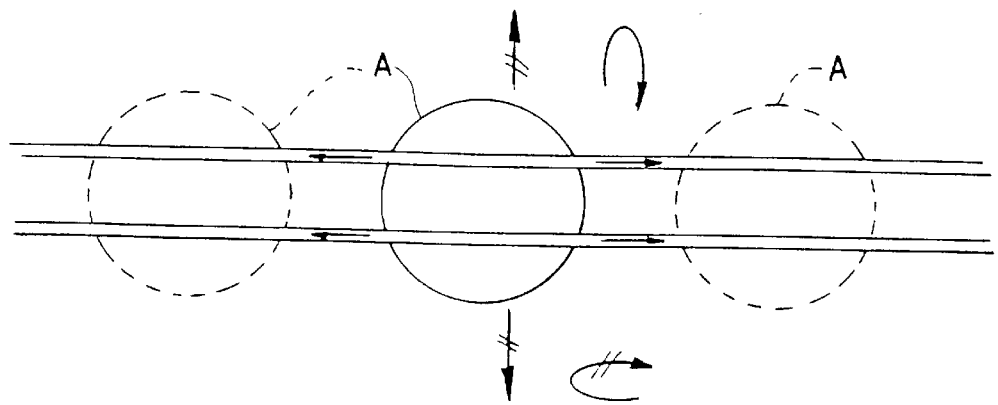
FIGS. 16 and 17 are diagrammatic representations of the translation and spin, respectively, in prostheses having parallel and crisscrossing channels.
Figure 17:
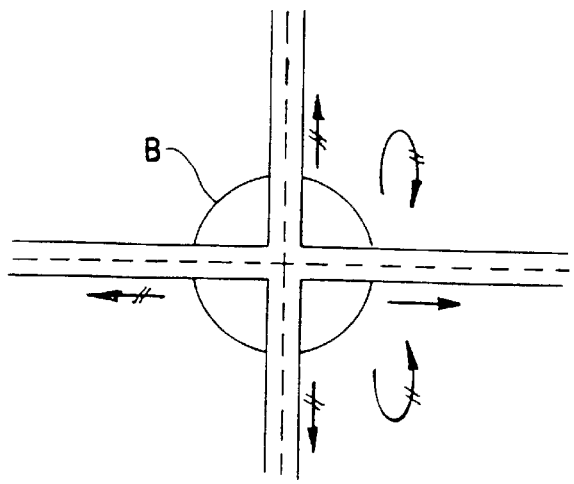
Figure 18A:
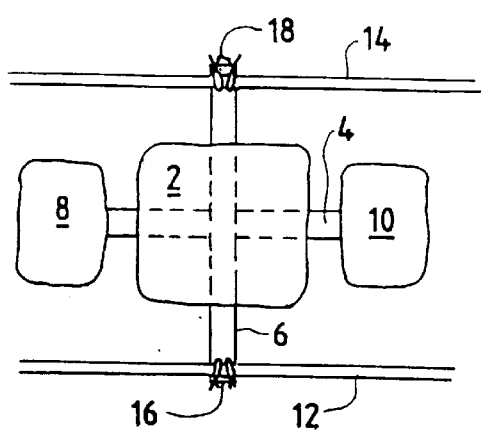
FIGS. 18A and 18B are diagramatic representations of a prosthesis suspended in accordance with the present invention both with and without buttressing to adjacent capsule.
Figure 18B:
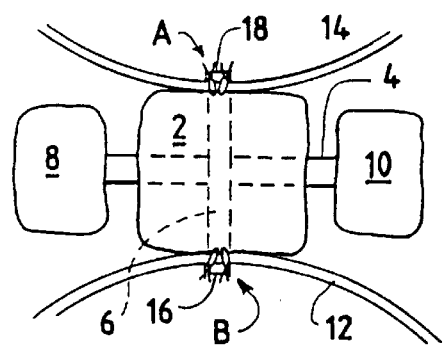

FIGS. 15(*a*) and 15(*b*) illustrate an alternative embodiment of the invention, as applied in metacarpal-phalangeal arthroplasty.

Turning first to FIG. 15(*a*), a body member in the form of metacarpal head component 500 has a channel 502 which passes through the body member, with a segment 503 of the central portion of the metacarpal head component cut away, in a fashion which creates chamfers 505.

This chamfer cut preparation of the distal metacarpal insures rotational stability of the metacarpal head component. In contrast, the preferred embodiment employs a straight perpendicular cut removal of the metacarpal head. The alternative embodiment adds rotational bone-implant stability vis-a-vis the chamber cuts, while maintaining ligamentous and capsular joint stability vis-a-vis the crisscrossing ligamentous means.

As shown in FIG. 15(*b*), body member 500 is press-fit onto the distal end of metacarpal 504 which has been prepared for this purpose. A drill (not shown) is passed through channel 502, across the cut-away portion through the bone residing therein and out of the other end of the channel, to form a first channel. A second channel 506 is then drilled substantially perpendicularly to first channel 502, through the portion of the metacarpal bone at the level of body member 500. Consistent with the design of the preferred embodiment, the proximal phalanx base component 508 is fit to proximal phalanx 509 with its stem 511 fixed in place by conventional means. Ligamentous means 510 and 512 are passed through substantially perpendicular channels in the metacarpal head component 500 and the metacarpal bone 504 and ligamentous means 514 and 516 are passed through the substantially perpendicular channels of the proximal phalanx base component. As in the preferred embodiment, the crisscrossing channels of the alternative embodiment may be intersecting or non-intersecting. All of the ligamentous means are then attached to adjacent ligaments and capsule, just as in the preferred embodiment. Thus, while the alternative design embodiment employs chamfer cuts, the inventive crisscrossing ligamentous means are also employed. In doing so, implant-bone interface rotational stability is improved, yet the inventive perpendicular capsular-ligament suspension-restraint mechanism is maintained.

It should be recognized that, while the invention has been described in relation to a preferred embodiment thereof, those skilled in the art may develop a wide variety of structural details without departing from the principles of the invention. Accordingly, the appended claims are to be construed to cover all equivalents falling within the scope and spirit of the invention.

The invention claimed is:

1. A surgically implantable bone prosthesis other than a carpal bone prosthesis comprising:

one or more biocompatible, medically inert body members contoured to resemble the shape of a bone, bones, or a portion of a bone or bones which are to be replaced by the prosthesis; and at least two ligamentous means for restraining the one or more body members along at least two crisscrossing axes which pass through each body member, and cross within the body member the body member or members including at least one channel passing therethrough, positioned along at least one of the crisscrossing axes.

2. The bone prosthesis of claim 1 in which each body member is made from a material chosen from the group consisting of ceramic, titanium, or stainless steel alloys.

3. The bone prosthesis of claim 1 in which each body member comprises a non-ceramic substrate with a ceramic or other biocompatible, medically inert coating.

4. The bone prosthesis of claim 1 in which the bone, bones, or portion of bone or bones is chosen from the group consisting of: proximal-interphalangeal joint, metacarpal-phalangeal joint, carpometacarpal joint, total wrist replacement, radial head, total elbow replacement, shoulder hemiarthroplasty, total shoulder, total hip, hemi-ankle, total ankle, total knee replacement, hip hemiarthroplasty, and metatarsal-phalangeal joint.

5. The bone prosthesis of claim 1 in which the restraining means comprise ligamentous means passing through the channels.

6. The bone prosthesis of claim 1 in which the ligamentous means are attached to adjacent bone, capsule, or ligament.

7. The bone prosthesis of claim 6 in which the ligamentous means have an open pore surface which is tissue ingrowth receptive for anchoring the ligamentous means within the channels.

8. The bone prosthesis of claim 1 in which the inert body member is configured to accept a portion of the native bone so that at least one of the crisscrossing axes passes through a channel formed through the portion of native bone.

9. The bone prosthesis of claim 1 in which selected areas of the body member include means for ingrowth adhesion.

10. The bone prosthesis of claim 1 in which selected areas of the body member include means for ligament ingrowth adhesion.

11. The bone prosthesis of claim 1 in which selected areas of the body member include means for capsule or ingrowth adhesion.

12. The bone prosthesis of claim 1 in which selected areas of the body member include means for bone ingrowth adhesion.

13. The bone prosthesis of claim 5 in which the ligamentous means comprise native tissue.

14. The bone prosthesis of claim 5 including only two channels in each body member in which ligamentous means pass through the two channels and are attached to adjacent bone, capsule, and/or ligament.

15. The bone prosthesis of claim 6 in which the ligamentous means are anchored within the channels with adhesive.

16. The bone prosthesis of claim 5 in which the restraining means comprise ligamentous means secured to the periphery of each body member along the two crisscrossing axes.

17. The bone prosthesis of claim 5 in which at least two of the channels physically intersect within each body member.

18. The bone prosthesis of claim 5 in which at least two of the channels do not physically intersect within each body member.

19. The bone prosthesis of claim 5 in which there are only two channels within each body member.

20. The bone prosthesis of claim 16 in which the ligamentous means are secured to the outer periphery of each body member by eyelets.

21. The bone prosthesis of claim 5 in which in which the edges of the channel openings are rounded.

22. The bone prosthesis of claim 5 in which the channels have a porous coating.

23. The bone prosthesis of claim 5 in which the ligamentous means are in the form of a rounded cord.

24. The bone prosthesis of claim 5 in which the channels are ovoid in cross-section.

25. The bone prosthesis of claim 1 in which the axes are substantially perpendicular.

26. The bone prosthesis of claim 5 in which at least two of the channels physically intersect within a body member.

27. A method for replacing a damaged bone or portion of a bone in a synovial or diarthroidal joint comprising:

removing the damaged bone or portion of a bone;

positioning a biocompatible, medically inert body member contoured to resemble the shape of the bone which it is to replace at the site formerly occupied by the damaged bone, the body member having at least two crisscrossing channels which cross within the body member; and restraining the body member along at least two axes passing through the channels.

28. The method of claim 27 in which ligamentous means are used to restrain the body member.

29. The method of claim 28 in which the ligamentous means have an open pore surface which is tissue ingrowth receptive.

30. The method of claim 28 in which the ligamentous means are anchored within the channels by adhesive, by a porous ingrowth coating, or by both adhesive and a porous ingrowth coating.

31. The method of claim 27 in which the ligamentous means are anchored within the channels by means of adhesive.

32. The method of claim 27 in which the channels are ovoid in cross-section.

33. The method of claim 27 in which the edges of the channel openings are rounded.

34. The method of claim 27 in which the channels have a porous coating.

35. The method of claim 28 in which the ligamentous means are flat.

36. The method of claim 28 in which the ligamentous means are in the form of a rounded cord.

37. A surgically implantable bone prosthesis comprising:
a biocompatible, medically inert body member contoured to resemble the shape of the bone which it is to replace; and
means for restraining the body member along crisscrossing axes which pass through the body member,
the body member including at least two channels passing therethrough along the axes and the restraining means comprising ligamentous means passing through the channels.

38. The bone prosthesis of claim 37 including adjacent bone and capsule in which the restraining means comprise ligamentous means attached to adjacent bone and capsule which pass through the body member within the two channels.

39. The bone prosthesis of claim 37 in which the ligamentous means have an open pore surface which is tissue ingrowth receptive for anchoring the ligamentous means within the channels.

40. The bone prosthesis of claim 37 in which the ligamentous means comprise native tissue.

41. The bone prosthesis of claim 37 in which at least two of the crisscrossing channels intersect.

42. The bone prosthesis of claim 37 in which the crisscrossing channels do not intersect.

43. A method for replacing a damaged bone in a human with a bone prosthesis comprising:
removing the damaged bone;
positioning a biocompatible, medically inert body member contoured to resemble the shape of the bone which it is to replace at the site formerly occupied by the damaged bone, the body member having at least two crisscrossing channels which cross within the body member; and
permanently restraining the body member along at least two axes passing through the crisscrossing channels.

44. The method of claim 43 in which the body member is restrained by ligamentous means anchored within the channels by adhesive, by porous coating ingrowth or by both adhesive and porous coating ingrowth.

45. The method of claim 43 in which the biocompatible, medically insert body member is buttressed to adjacent capsule.

46. A three component total wrist arthroplasty comprising:
a proximal component adapted to be rigidly affixed to the radius;
a distal component adapted to be rigidly affixed to the remaining distal carpus and metacarpals; and
a middle component having at least two crisscrossing channels passing therethrough and means passing through the channels for suspending and restraining the middle component between the proximal and distal components.

47. A surgically implantable bone prosthesis comprising:
one or more biocompatible, medically inert body members contoured to resemble the shape of a bone, bones, or a portion of a bone or bones which are to be replaced by the prosthesis, with selected areas of the body members having means for ingrowth adhesion; and
means for restraining the one or more body members along at least two crisscrossing axes which cross within the body member, the body member or members including at least one channel passing therethrough, positioned along at least one of the crisscrossing axes.

48. The bone prosthesis of claim 47 in which the selected areas of the body member include means for ingrowth adhesion.

49. The bone prosthesis of claim 47 in which the selected areas of the body member include means for ligament ingrowth adhesion.

50. The bone prosthesis of claim 47 in which the selected areas of the body member include means for capsule ingrowth adhesion.

51. The bone prosthesis of claim 47 in which the selected areas of the body member include means for bone ingrowth adhesion.

52. A surgically implantable b,one prosticsis comprising:
one or more biocompatible, medically inert body members contoured to resemble the shape of portions of a bone or bones which are to be replaced by the prosthesis; and
means for restraining each of the one or more body members along at least two crisscrossing axes, with at least one of the crisscrossing axes passing through each body member and with a channel in the body member positioned along the at least one of the crisscrossing axes; and
wherein at least one of the crisscrossing axes passes through the remaining portion of the bone and the at least two crisscrossing axes cross within the remaining portion of the bone and/or within the body member.

53. The bone prosthesis of claim 52 in which selected areas of the one or more body members have means for ingrowth adhesion.

* * * * *

UNITED STATES PATENT AND TRADEMARK OFFICE
CERTIFICATE OF CORRECTION

PATENT NO. : 5,888,203
DATED : March 30, 1999
INVENTOR(S) : Robert Goldberg

It is certified that error appears in the above-identified patent and that said Letters Patent is hereby corrected as shown below:

Column 7, line 7, after "accordance" insert --with--

Column 14, line 40, delete the repeated pharse "in which"

Column 16, line 2, delete "insert" and insert --inert--

Column 16, line 39, delete "b,one prosticsis" and insert --bone prosthesis--

Signed and Sealed this

Eighteenth Day of January, 2000

Attest:

Attesting Officer

Q. TODD DICKINSON

*Commissioner of Patents and Trademarks*